United States Patent [19]
Chelsky et al.

[11] Patent Number: 5,856,083
[45] Date of Patent: Jan. 5, 1999

[54] LAWN ASSAY FOR COMPOUNDS THAT AFFECT ENZYME ACTIVITY OR BIND TO TARGET MOLECULES

[75] Inventors: Daniel Chelsky, Moylan, Pa.; Jonathan J. Burbaum, Cranbury, N.J.

[73] Assignee: Pharmacopeia, Inc., Princeton, N.J.

[21] Appl. No.: 553,056

[22] Filed: Nov. 3, 1995

Related U.S. Application Data

[63] Continuation-in-part of Ser. No. 436,120, May 8, 1995, abandoned, which is a continuation-in-part of Ser. No. 239,302, May 6, 1994, abandoned.

[51] Int. Cl.⁶ ....................................... C12Q 1/00
[52] U.S. Cl. .................. 435/4; 435/7.1; 435/7.2; 435/7.8; 435/177; 435/178; 435/182; 436/164; 436/169; 436/170
[58] Field of Search ............................ 435/4, 6, 7.1, 7.2, 435/7.21, 7.8, 174, 176, 177, 178, 968, 969, 182, 7.7; 436/518, 524, 528, 537, 164, 169, 170, 172, 529, 535

[56] References Cited

U.S. PATENT DOCUMENTS

| | | |
|---|---|---|
| 3,817,837 | 6/1974 | Rubenstein et al. . |
| 5,498,530 | 3/1996 | Schatz et al. . |
| 5,502,246 | 3/1996 | Sucholeiki . |
| 5,506,337 | 4/1996 | Summerton et al. . |
| 5,510,240 | 4/1996 | Lam et al. . |
| 5,565,324 | 10/1996 | Still et al. . |
| 5,565,325 | 10/1996 | Blake . |
| 5,576,436 | 11/1996 | McCabe et al. . |
| 5,601,922 | 2/1997 | Lerner et al. . |

FOREIGN PATENT DOCUMENTS

| | | |
|---|---|---|
| 9200091 | 1/1992 | WIPO . |
| WO 92/00091 | 1/1992 | WIPO . |
| 9402515 | 2/1994 | WIPO . |
| WO 94/02515 | 2/1994 | WIPO . |
| WO 94/08051 | 4/1994 | WIPO . |
| WO 94/28028 | 12/1994 | WIPO . |

OTHER PUBLICATIONS

Sambrook et al. "Molecular Cloning", Cold Spring Harbor Press Inc., 1989, pp. 6.3–6.5.
Jenkins, S.H., Journal of Immunological Methods, 150: 91–97, 1992.
Bailey et al, Journal of Pharmaceutical and Biomedical Analysis 5(7):649–658, 1987.

*Primary Examiner*—Patricia Duffy
*Attorney, Agent, or Firm*—Darby & Darby

[57] ABSTRACT

A lawn assay is described for determining compounds that affect enzyme activity or that bind to target molecules. Compounds to be screened are cleaved, and diffused from solid supports into a colloidal matrix. Enzymatic catalysis or binding to target molecules by the compounds is carried out in the matrix. Active compounds are found by monitoring a photometrically detectable change in a substrate, coenzyme, or cofactor involved in the enzymatic reaction, or in a labeled ligand bound to the target molecule, that produces a zone of activity associated with the compounds.

22 Claims, 7 Drawing Sheets

PC463767

| Time (h) | Av. Area | pmol/bead |
|---|---|---|
| 0.5 | 271882 | 43.6 |
| 1 | 431984 | 69.3 |
| 2 | 520253 | 83.1 |
| 4 | 562536 | 90.3 |
| 6 | 750539 | 120 |
| 8 | 755068 | 121 |
| 14 | 757987 | 122 |
| 18 | 823134 | 132 |
| 21 | 865130 | 139 |
| 24 | 918459 | 147 |
| STD | 356278 | 114.3 |

6,727 members

5,856,083

LAWN ASSAY FOR COMPOUNDS THAT AFFECT ENZYME ACTIVITY OR BIND TO TARGET MOLECULES

This application is a continuation-in-part of U.S. patent application Ser. No. 08/436,120, filed May 8, 1995 now abandoned, which is a continuation-in-part of U.S. patent application Ser. No. 08/239,302 now abandoned, filed May 6, 1994.

FIELD OF THE INVENTION

This invention relates to assays that screen many compounds for their effect on enzyme activity or their ability to bind to target molecules.

BACKGROUND OF THE INVENTION

To find lead compounds for drug discovery programs, large numbers of compounds are often screened for their activity as enzyme inhibitors or receptor agonists/antagonists. Large libraries of compounds are needed for such screening. As a result of developments in this field, it is now possible to simultaneously produce combinatorial libraries containing hundreds of thousands of small molecules for screening. With the availability such libraries, however, has come a need for large scale, rapid screening methods.

The use of microtiter plates has significantly improved screening of combinatorial libraries. The plates allow assays to be miniaturized and have provoked the development of automated liquid handling and detection instruments to improve throughput and reproducibility. Robotics have allowed integration of compound arraying, microtiter plate handing, liquid handling, data acquisition and data processing. Even when facilitated by robotics, however, the steps of weighing, distributing, dissolving and serially diluting compounds in microtiter plates are time consuming.

The availability of combinatorial libraries on polymer beads have simplified these processes. By synthesizing sufficient compound on each bead for a few assays, compound handling is reduced or eliminated. Furthermore, thousands of beads can be arrayed in a given assay, and the compounds on the beads detached by photolysis, or other cleavage methods, into the assay in the concentration desired. Assaying library beads in standard microtiter plates therefore results in substantial improvement over the conventional assaying of bulk synthesized compounds.

The advantages of the bead format, however, have not been fully realized. In particular, scanning thousands of microtiter plate wells for positive results can be time consuming. Also, when beads are assayed in a microtiter well, only low concentrations of compounds are obtained since each bead contains only a small amount of compound. There is a need, therefore, for a more efficient method of screening large combinatorial libraries on beads, or other solid supports. There is also a need for a method which can assay higher concentrations of compounds on beads.

WO94/02515 describes screening a library of beads immobilized on a substrate, such as agarose. Molecules are partially cleaved from the beads and diffuse through the substrate, where they contact receptors on the surface of melanocytes. This causes pigment aggregation or dispersion within the cells, providing a signal that indicates where molecules have bound. WO94/02515 also describes determining immunological binding by diffusing labeled molecules in a gel, and contacting the molecules with antibodies on a plate below the gel, or in a second gel. Unbound molecules must be washed away, and the label detected. WO 94/02515 does not describe any method for detecting molecules that affect the activity of enzymes. It also does not describe any method for detecting binding to proteins without washing steps, which are particularly difficult to perform when using gels. In addition, it does not describe any method for screening compounds for binding to receptors that is not dependent on a biological response within a cell.

SUMMARY OF THE INVENTION

The present invention relates to a lawn assay for identifying compounds that affect enzymatic catalysis, or that bind to target molecules. The assay involves the steps of:

a. providing an enzyme or a target molecule;

b. where an enzyme is provided, further providing a substrate for the enzyme, and where a target molecule is provided further providing a labeled ligand bound to said target molecule;

c. providing a plurality of solid supports, each of the supports having multiple copies attached thereto by a cleavable linker of a compound to be screened for its effect on enzyme catalysis or its ability to bind to the target molecule;

d. contacting the solid supports with a colloidal matrix and cleaving the compounds from the supports, either before or after the contacting step, so that the compounds diffuse into the colloidal matrix;

e. carrying out the enzymatic catalysis or binding of compounds to target molecule in the colloidal matrix; and f. monitoring a photometrically detectable change in:
  (1) the substrate, or a coenzyme or enzyme cofactor involved in the enzymatic reaction, or
  (2) in the labeled ligand to determine a zone of activity in the matrix associated with one or more of the compounds.

DETAILED DESCRIPTION OF THE INVENTION

Figure 1A:
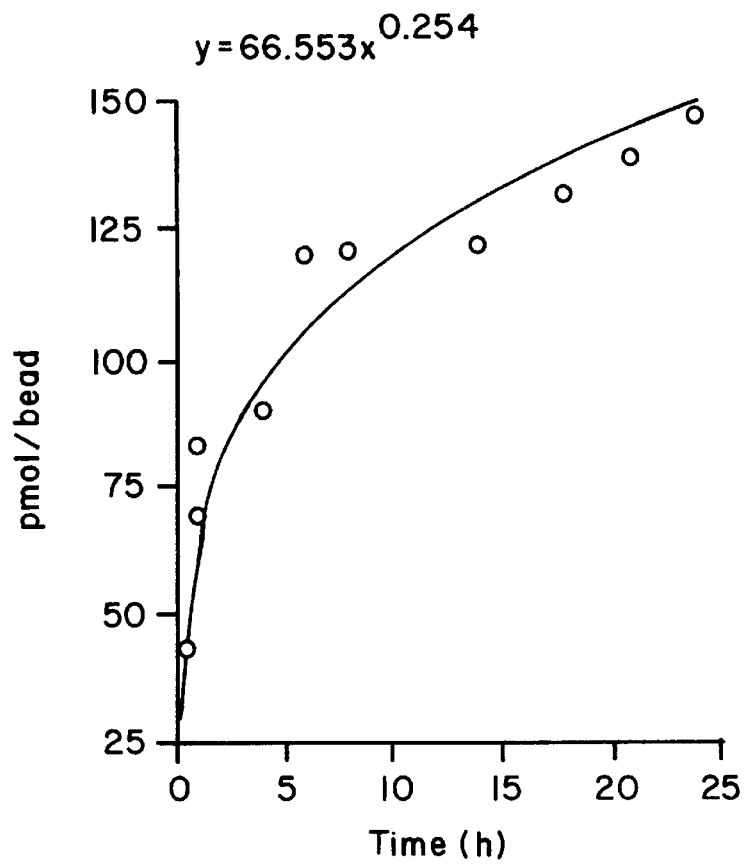
FIG. 1 is a graph showing results of an HPLC analysis of solute ("PC463767") released from photocleaved beads as the amount of photolysis is increased. The structure of the compound PC463767 is also shown, as is a table of the results that are included in the graph.

All patent applications, publications, or other references that are listed herein are hereby incorporated by reference.

In one embodiment of this invention, a library of solid supports, preferably beads, is screened for the ability of compounds on the supports to affect the activity of an enzyme. Using the invention, supports containing the active compounds are quickly and easily located merely by viewing zones of inhibition in a matrix. In this embodiment, the solid supports are contacted with a colloidal matrix, such as agarose. The compounds are linked to the supports by a cleavable linker and released, e.g., by exposure to light. As they slowly diffuse out of the solid supports, zones of high concentration of the compounds are created in the supports' immediate vicinity. The compounds contact enzyme contained in the matrix. Substrate is contacted with the matrix and reacts with the enzyme. Conversion of substrate to product is measured by monitoring a photometric change in the substrate, or in a coenzyme or cofactor involved in reaction. For example, the substrate can be fluorogenic, i.e., becoming fluorescent when converted to product. In this case, compounds that are active inhibitors of the enzyme reaction are detected as dark zones of inhibition. The less active, or inactive, compounds are contained in the lighter areas.

Using this assay, positive results from an assay of a combinatorial library can be detected very quickly. Furthermore, compound activity can be quantitated by e.g., comparing the sizes of zones of activity. Once zones of activity have been determined, the relevant supports at the center of the zones can be located and the active compounds on those supports identified. The invention thus allows large libraries of compounds to be quickly and easily screened. Very little effort is required to array the solid supports or assay the compounds released from the supports.

In another embodiment, the lawn assay is used to determine compounds that bind to a target molecule, and thereby affect a detectable signal generated by a labeled ligand bound to the target molecule. This assay allows screening of compounds that, e.g., act as agonists or antagonists of a receptor, or that disrupt a protein:protein interaction. It also allows detection of binding to DNA, RNA, or complex carbohydrates. For example, neurokinin receptor binds to a 7-nitrobenz-2-oxa-1,3-diazol-4-yl (NBD)-labeled peptide ligand. The labeled ligand has the following formula: PhCO-2,4-diaminobutyric acid(gamma-NBD)ala-D-trp-phe-D-pro-pro-Nle-NH2. NBD is a fluorophore, and binding of the labeled ligand to the neurokinin receptor increases NBD's fluorescence. When a compound displaces the NBD-labeled ligand from the neurokinin receptor, fluorescence of the NBD fluorophore is reduced (G. Turcatti, H. Vogel, A. Chollet (1995) *Biochemistry* 34, 3972–3980). A library of solid supports can be screened for compounds that bind to neurokinin receptor in a colloidal matrix using the method of the invention. Active compounds are found in zones of decreased fluorescence. As another example, a radioligand (tritium or $^{125}$Iodine-labeled) can be used to screen for compounds binding to a receptor with the assay of invention by using Scintillation Proximity Assay beads (SPA™, Amersham Corp.) or scintillant coated plates (Flashplates™, Dupont NEN Research Products). Receptor is bound to SPA™ beads or to a Flashplate™ surface and radiolabeled ligand in a colloidal matrix is allowed to interact with the receptor. This interaction brings the radiolabel in close proximity with the scintillant and results in a scintillation signal. The signal can be detected using x-ray film, or other commercially available film that is specifically designed to detect tritium dependent scintillations. Compounds released into the matrix from the solid supports that bind to receptor and displace the radioligand reduce the scintillation signal, i.e., result in a zone of reduced scintillation. The receptor used in the assay can be e.g., membrane-bound, tethered to a solid phase, or solubilized.

When using the assay to find compounds that affect enzyme activity, it is preferred that the substrate or the product of the enzymatic reaction generate a detectable signal. The difference in signal between the substrate and product should be significant. It is particularly preferred to use a substrate which generates little or no signal, and which converts to a product which generates a strong signal. If the substrate produces detectable signal which cannot be distinguished from that of the product, it can create background noise, thereby reducing the overall sensitivity of the assay. For this reason, non-fluorescent substrates that convert to fluorescent products, i.e., fluorogenic substrates, are preferred. One well known fluorogenic substrate is fluorescein diacetate, which converts to fluorescein in the presence of an esterase, such as carbonic anhydrase. Other fluorogenic substrates include 7-amino-trifluoromethyl coumarin (AFC), 4-trifluoromethylumbelliferyl (HFC), 7-amino-4-methylcoumarin (AMC) and 4-methoxy-2-naphthylamine (MNA).

Alternately, a fluorescent substrate can be used that converts to a product having different excitation and emission characteristics. By using band-pass filters so that only the product is excited and detected, the substrate can be effectively screened out. An example of such a fluorescent substrate is peptidyl-aminomethylcoumarin, which is converted by an appropriate protease, such as thrombin, to free aminomethylcoumarin. The free aminomethylcoumarin excites and emits at different wavelengths than does the peptidyl-aminomethylcoumarin (S. Kawabata et al. (1988) *Eur. J. Biochem.* 172, 17).

It is also possible to use a substrate containing internally quenched fluorophores that become fluorescent when converted to product. Such quenching reactions are well known (E. Matayushi et al. *Science* 247, 954). For example, a peptide substrate can be produced having two fluorophores at opposite ends, one absorbing the fluorescence of the other. The substrate therefore emits a negligible amount of light. Upon cleavage of the peptide by a suitable protease, the absorbing fluorophore is released and no longer quenches the other fluorophore, resulting in an increase in fluorescence. One such substrate is 4(dimethylaminophenylazo)-benzoic acid (DABCYL)-Gabu-glu-arg-met-phe-leu-ser-phe-pro-5-[(2-aminoethyl)amino]napthalene-1 sulfonic acid (EDANS), which when cleaved by an aspartyl protease (e.g., plasmepsin 11 of *Plasmodium falciparum*) becomes fluorescent. In screening a library of aspartyl protease inhibitors using the assay of the invention, those that are active inhibit cleavage of the substrate, allowing quenching to be maintained. Active compounds are found in dark zones of inhibition.

Fluorescence can be detected, e.g. using a field format fluorescence detection instrument, such as FluorImager™ from Molecular Dynamics. This type of fluorimeter is capable of determining fluorescence over a large area. It is also possible to detect fluorescence using a CCD camera and to transfer the image data to a computer. The image can be generated by illumination of the fluorophore with light of the wavelength that specifically excites it. Detection can be optimized by using a bandpass filter between the camera and the assay that is specific for the emission wavelength of the fluorophore.

Assays that measure a change in fluorescence are preferred as they are believed to result in the greatest sensitivity. Any method, however, can be used that measures a change in signal from one of the compounds involved in the reaction as a result of conversion of the substrate to product, or displacement of the labeled ligand from the target. An example of an assay for compounds that affect a chromogenic substrate, p-nitrophenylphosphate, is described in the examples. It is also possible, for example, to measure a change in absorbance. For example, NADP is a common cofactor in many enzymatic reactions. Absorbance changes as NADPH is converted to NADP by, for example, neutrophil NADPH oxidase (such as during an oxidative burst associated with an immune response). This change can be monitored to determine zones of inhibition for compounds that inhibit this and other enzymes that use NADP, NADPH, NAD, and NADH as co-factors. The sensitivity of assays of the invention that measure a change in absorbance is believed to generally be lower than those that measure a change in fluorescence.

Other examples of detectable changes resulting from conversion of substrate to product include chemiluminescent changes and scintillation changes. Scintillation changes can be detected as described above for receptor binding with the exception that a substrate is attached to the scintillant (i.e., to the bead or plate containing scintillant). For example, a radioactive reagent, such as tritiated farnesyl pyrophosphate, can be added to the substrate by an enzyme such as farnesyl protein transferase. Transferase inhibitors prevent addition of the tritiated farnesyl pyrophosphate to the substrate, resulting in a reduction in detectable scintillations; i.e., transferase inhibitors are found in zones of reduced scintillation. In an alternative assay, removal of the radioactive portion of a substrate attached to the scintillant, such as by cleaving with a protease, releases the radiolabeled portion (i.e., moves it away from the scintillant). In such an assay, protease inhibitors cause an increase in scintillation, i.e., are found in zones of increased scintillation. As noted above, the scintillation signal can be detected using x-ray film, or film that is specifically designed to detect tritium dependent scintillations.

In the embodiment of the invention for assaying binding to a target molecule, a labeled ligand provides a signal that indicates such binding. The label is preferably a fluorescent moiety that alters its signal as a result of target molecule binding. Examples of such fluorescent moieties are NBD and 5-(dimethylamino)-1-naphthalenesulfonyl (Dansyl) chloride.

Colloidal matrixes that are useful in the invention include silica gel, agar, agarose, pectin, polyacrylamide, gelatin, starch, gellan gum, cross-linked dextrans (such as Sephadex™) and any other matrix that allows diffusion of compound from the solid supports in a limited region. Low melting-temperature agarose is preferred, generally in an amount of 0.5–2.0%, wt./vol. The colloidal matrix can be chosen to obtain a desired rate of diffusion. It is generally preferred to use a matrix that allows a high concentration of compounds to be easily obtained.

In carrying out the invention to determine compounds that affect enzyme activity, the solid supports are preferably embedded in a matrix containing the relevant enzyme. Following cleavage, compound diffuses from the support into the matrix and contacts the enzyme. Substrate is then added and, as it diffuses into the colloidal matrix, active compounds inhibit conversion to product. By following such a procedure, compounds to be screened are allowed to interact with enzyme before the enzyme contacts substrate. This is believed to be advantageous because it allows compounds the best opportunity to inhibit the enzyme, and thus results in the clearest zone of inhibition.

It is also possible, however, to embed the solid supports in a matrix that contains dispersed substrate. Following cleavage, the matrix can be contacted with enzyme. This procedure is not believed to be as sensitive since the compounds may not efficiently bind to the enzyme.

To practice the invention, however, it is not necessary that the solid supports be embedded in the matrix. They can also be applied to the matrix's surface and the compounds allowed to diffuse into the matrix. This can be done, for example, by arraying the solid supports on the surface of a stretched sheet of plastic film (e.g., Parafilm™), and then applying the sheet to the surface of the matrix.

In assaying for compounds that affect enzyme activity, it may be desirable to use two colloidal matrixes. For example, one matrix can contain enzyme and beads and the other can contain substrate. Contacting the surfaces of the matrixes to each other allows the substrate to come into contact with the enzyme. However, any suitable method may be used to contact the substrate, enzyme, and compounds in the colloidal matrix. For example, it is possible to add a solution of substrate over the surface of a matrix containing enzyme and embedded supports. Adding solution is preferred when, e.g., the substrate interferes with detection. Solution containing the substrate can be removed prior to determining the zones of activity.

When using the assay of the invention to screen for binding to a target molecule, there is generally no need for more than one matrix. A matrix contains the target molecule bound to the labeled ligand which emits a detectable signal indicating binding to the target molecule. Compounds from the solid supports are diffused into the matrix, preferably from embedded supports using photolysis. Alternatively, however, labeled ligand can be diffused into the matrix from a second matrix (or liquid layer) after release of the compounds in the matrix. This allows the compounds to contact the receptor before interaction with the labeled ligand, which can be advantageous.

Compounds can be cleaved from the solid supports either before or after the supports are contacted with the colloidal matrix. For example, solid supports may contain acid cleavable linkers, as further described below. These linkers can be cleaved in a gaseous acidic atmosphere before placing the supports on the matrix. The compounds, although cleaved, remain on the surface of the supports and diffuse into the matrix when the supports are placed on it. It is even possible to cleave the compounds prior to pouring low-melt liquid agarose over the solid supports. While some of the compounds will be washed away, sufficient compound can remain on the support's surface to result in a recognizable zone of activity.

Where the compounds are cleaved after the beads are embedded in the colloidal matrix, it is preferred to use photolysis, e.g., cleaving by exposure to UV light. By adjusting light exposure, it is possible to control the amount of compound that diffuses into the matrix. If more light is applied, by increasing intensity or duration, more cleavage results, in turn releasing more compound into the matrix. This allows the amount of active compound released to be adjusted, so that zones of activity are only produced for compounds that are most active. The amount of compound released can also be optimized to produce zones that are most distinct.

Any suitable solid support can be employed in the method of the invention. Such supports include beads, pellets, disks, fibers, and gels. They also include particles such as cellulose beads, controlled pore-glass beads, silica gels, and polystyrene beads (optionally cross-linked with divinylbenzene and optionally grafted with polyethylene glycol and optionally functionalized with amino, hydroxy, carboxy, or halo groups). Additional supports include grafted co-poly beads, poly-acrylamide beads, latex beads, dimethylacrylamide beads (optionally cross-linked with N,N'-bis-acryloyl ethylene diamine), glass particles coated with hydrophobic polymers, etc., (i.e., having a rigid or semi-rigid surface) and soluble supports such as low molecular weight non-cross-linked polystyrene. Divinylbenzene-crosslinked, polyethyleneglycol-grafted polystyrene type beads are preferred, such as TentaGel S-NH$_2$® beads (Rapp Polymere, Tubingen, Germany).

The solid supports can be in a random arrangement, or in an ordered one. Preparing a random arrangement of solid supports requires little effort. For example, a library of beads can be suspended in a solvent, such as ethanol, and deposited on the bottom of a petri plate. After the solvent has completely evaporated, a layer of agarose containing the relevant enzyme or target molecule can be poured over the beads. On the other hand, an ordered array can be used to space beads apart and allow easier identification of those that are active. In one example of an ordered array, beads are arrayed on a rigid template, such as a thin glass disk having tapered holes. The tapered holes are sized to allow only single beads to settle into them. Beads are suspended in a solvent, such as ethanol, and washed over the top of the template to fill each hole with one bead. The beads can then be cleaved in the dry state, and the template set down on the colloidal matrix. Capillary action wets the beads, facilitating diffusion of the cleaved compounds into the matrix. Zones of activity can be observed immediately below beads containing active compounds. It is possible to remove the template prior to detecting zones of activity if an image of the template on the matrix is made. This image can later be used to correlate the zones of inhibition in the matrix with the positions of beads on the template.

Ordered arrays also may be useful in identifying the compounds on supports that are associated with zones of activity. Specifically, the array can be ordered so that the position of the solid support on the array corresponds to the identity of the compound. Thus, once an assay has been carried out, and the position on the array determined for a support carrying an active compound, the identity of that compound can be easily determined.

Preferably, however, the identity of active compounds is determined using the encoding system described in WO 94/08051 and in parent applications Ser. Nos. 08/436,120 now abandoned and 08/239,302 now abandoned. In this system, chemical tags encoding the identity of the compounds are applied to the solid supports. The identity of the compound on a given support can be determined by detaching the chemical tags from the support, identifying the tags by, e.g., gas chromatography, and correlating the pattern of tags with the identity of the compound. Once a zone of activity is found, the bead at the center of the zone can be extracted, and the identity of the compound on the bead decoded by this method.

The assay is preferably carried out so that there is slow diffusion of the compound from the solid support following cleavage. This results in a high concentration of compound in the vicinity of the bead. Thus very little compound is required to cause a distinct zone of activity. Most of the compound remains on the support for any subsequent assays that are required. Such further assays may be needed if more than one solid support is found in the zone of activity. It may then be necessary to retest the supports from the zone to determine which releases the active compound. Reassaying may be required as a matter of course if many thousands of beads are screened at high density. Reassaying may also be desirable to test for selectivity, i.e. to determine which active compounds are inactive in a second assay that tests for a different property.

With combinatorial libraries containing thousands of related compounds, many compounds may be found that have some degree of activity. It therefore may be to useful to use the assay of the invention to distinguish the most potent compounds. In the assay, if the amount of compound released from each support is approximately the same, potent compounds have a detectable effect further from the bead than weak compounds do, at any given time. Thus, the more active compounds create a larger zone of activity. Furthermore, the zone of activity of the most active compounds lasts longer. Thus, it is possible to quantitate the activity of the compound eluted from the solid support by the size of the zone of activity, as well as by the duration of the zone following cleavage.

Reducing photolysis time reduces the amount of compound released from the support. As the concentration of the compounds is lowered, those that are less active become more difficult to detect. As a result, the number of active compounds drops. In experiments described in the Examples, compounds that were detectable at the shortest elution times, i.e., that were most potent, were also identified as most potent using conventional solution-phase screening. The activity of the inhibitors was found to correlate with the size and duration of the zone of activity: the most potent compounds produced the largest zones for the longest time, for any given amount of photolysis.

When assaying a library containing many active compounds, it may be desirable to screen using a low density of solid supports, i.e., a low number of supports per cm$^3$ of matrix. While requiring more assays to screen the entire library, it is less likely that supports will have to be retested to determine which contains the active compound. The present inventors believe that screening a large library containing many active members at a low density is often more efficient than screening at high density, since rescreening supports is time consuming. The optimum density for screening can be determined for a given library by comparing the throughput in the initial assay with the effort required to retest active supports. Other factors which affect optimum screening density include the cost of the target and the size of the library.

When several large libraries are available for testing, it may be advantageous to incompletely evaluate each library by "scouting" each at high density for active compounds. Screening at high density allows one to statistically evaluate the number and potency of active compounds in each library. Libraries which contain the most active compounds can be more thoroughly tested.

If the proportion of active compounds screened in the assay is high, a second assay of the active compounds may be performed to choose those that should be further evaluated. The second assay can determine whether there is cross reactivity with other targets, i.e., a "selectivity screening". For example, a given library of compounds can be screened for activity against HIV protease, a member of the aspartyl protease family, using DABCYL-gAbu-Ser-Gln-Asn-Tyr-Pro-Ile-Val-Gln-EDANS. Compounds found active in the initial assay can be counter-screened against a second, different aspartyl protease, such as cathepsin D. Alternately, all compounds screened in the assay for activity against HIV protease could be simultaneously screened in the counter assay.

In the embodiment of the invention that tests for compounds that affect enzyme activity, it is preferred to test for inhibitors. It is also possible, however, to test for compounds that interfere with proteins that inhibit enzyme activity. In such an assay, the most active compounds prevent enzyme inhibition, resulting in more enzymatic catalysis. Thus, when a fluorogenic substrate is used active compounds result in a brighter zone of activity. For example, P16 is a known protein inhibitor of cyclin-dependent kinase-4 (Cdk-4). Using the assay of the invention, Cdk-4, Cyclin C1, p16, a fluorogenic substrate and a library of beads to be screened can be included in a layer of low-melt agarose. Following photocleavage, and after allowing sufficient time to convert substrate to product, the gel can be subjected to an electrophoretic separation. Product migrates to the anode, where it is preferably trapped on an anode filter. The location of product on the filter indicates the position in the gel of compound that disrupts p16 inhibition of Cdk4.

In another embodiment of the invention, an electrophoretic procedure is used to separate substrate from product to increase the sensitivity of the assay. In this embodiment, a substrate is used which changes charge when converted to product. An example of such a substrate is the peptide leu-arg-arg-ala-ser-leu-gly attached to a fluorophore, sold commercially as Pep-Tag™ (Promega Corp.). Protein kinase A (PKA) phosphorylates this substrate, which has net $^{+}1$ charge, to form a phosphopeptide which has a net $^{-}1$ charge. A lawn assay is performed in which PKA is contacted in a colloidal matrix with substrate and a library of potential inhibitors. An electrophoretic separation is then carried out across the width of (i.e., perpendicular to) the matrix. The phosphopeptide (i.e., product) moves towards the anode, and the dephosphopeptide (i.e., substrate) moves towards the cathode. If a membrane is applied to one or both sides of the matrix during electrotransfer, electroblotting can be achieved. For example, the phosphopeptide can be electroblotted to a suitable membrane, such as an Immobilon™ CD membrane. Alternately, the dephosphopeptide can be electrotransferred to an appropriate paper, such as Whatman™ 3MM paper. In another embodiment, the substrate and product can be chosen so that one is neutral and one is charged. Application of the electrophoretic field will remove the charged moiety. The resulting matrix will contain only the neutral moiety, thereby allowing detection of compounds that affect the conversion to product. The position of the bead containing the active compound can be determined by fluorescent imaging of the substrate or product, using, e.g., photography or video imaging. This technique increases sensitivity of the lawn assay by separating fluorescent substrate from fluorescent product, concentrating the fluorescent image, and by eliminating compounds from the matrix that might cause background signal. Other protein kinases and phosphatases such as protein kinase C, cyclin dependent kinases, MAP kinases, and inositol monophosphatase can also be used with appropriate substrates in this method. A protease can also be screened by this method by using a substrate consisting of an appropriate peptide linked to a labelling moiety, such as a fluorophore. The peptide sequence is chosen so that the substrate and product will migrate differentially in an electric field.

The compounds to be tested are linked to the solid support through a cleavable linker. In a preferred embodiment, the linker is photocleavable. This is especially advantageous where the support is cleaved after being embedded in a matrix. Photocleavable linking groups include:

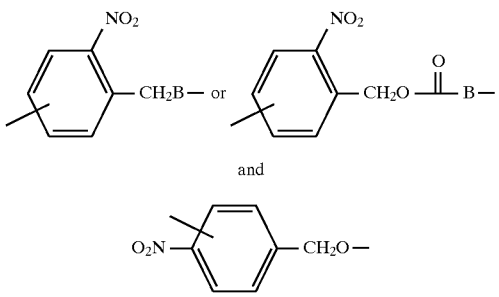

Where a photocleavable linker is used, the supports should be protected from light prior to use.

Other examples of linkers and the relevant cleavage reagents are described in WO 94/08051 and parent applications Ser. Nos. 08/436,120 and 08/239,302, which have been incorporated by reference herein. Photocleavable linkers are further described in Barany et al. (1985) *J. Am. Chem. Soc.* 107, 4936. Acid cleavable linkers are further described in Chao et al. (1994) *J. Am. Chem. Soc.* 116, 1746. Ammonia cleavable linkers are described in Kaiser et. al. (1982) *J. Org. Chem.* 47, 3258. Acid cleavable linkers and ammonia cleavable linkers allow cleavage by exposing the solid supports to a gaseous atmosphere, e.g. before the supports are applied to the colloidal matrix.

Enzymes that can be used in the assay include, but are not limited to, the following:

Acid Phosphatase
Activated Protein C
Alkaline Phosphatase
Aminopeptidases B & M
Amyloid A4-Generating Enzyme
Angiotensinase
Aryl Sulfatase
β-Galactosidase
β-Glucosidase
β-Glucuronidase
Calpains I & II
Cathepsins B, C, D, & G
Cholinesterase
Chymotrypsin
Collagenase
Dipeptidyl Peptidases I–IV
Elastase
Endothelin Converting Enzyme
Factor Xa
Factor XIa
Factor XIIa Df-Protease
Furin
γ-Glutamyltranspeptidase
Granzymes A & B
HIV Protease
IL-1B Convertase
Kallikrein
Lysozyme
Mast Cell Protease
Peroxidase
Plasmin
Prohormone Convertase γ ANP Precursor Processing Enzyme Renin Spleen Fibrinolytic Proteinase Staphylocoagulase Thrombin Tissue Plasminogen Activator Trypsin Tryptase Urokinase The invention is further illustrated by the Examples below, which are intended to exemplify the invention, not limit its scope.

EXAMPLES

Methods and Materials

The lawn assay was performed in Petri plates using two layers of agarose, each about 1.5 mm thick. The first layer contained TentaGel S-NH$_2$™ beads and enzyme. The Tenta-Gel S-NH$_2$™ beads had compounds to be screened attached thereto by a o-nitrobenzyl photocleavable linker and chemical tags attached for identifying the compounds, prepared according to methods described in WO 94/08051, parent applications Ser. Nos. 08/436,120 and 08/239,302, and H. Nestler et al. (1994) *J. Org Chem.* 59, 4723. The beads were either placed on the Petri plate and agarose poured over them, or beads and agarose were first mixed and then poured together onto the plate. A second layer of agarose containing the fluorescein diacetate was contacted with the first layer to initiate the reaction.

More specifically: 50 mM sodium phosphate, pH 7.4, was used as a buffer and all solutions equilibrated in a 37° C. water bath immediately prior to initiation of the assay. 0.1 mL of 5.3 µM bovine carbonic anhydrase (Sigma Chemical Co.) was diluted in 2.15 mL of buffer, and 1.25 mL of 2.5% low-gelling agarose added (SeaPlaque™, FMC BioProducts). Library beads suspended in methanol were added to a 6 cm polystyrene petri plate and, if necessary, distributed with a flat pipette tip. After evaporation of the methanol, the agarose solution was poured over the beads and allowed to gel at room temperature for 2–3 minutes. (Alternatively, dry beads can be added to a mixing tube, and then enzyme and agarose added; the mixture is then vortexed and poured.) The plate was then placed under a long wave (360 nm) UV lamp (Blackray™ UVP, Inc.) for from 5 sec to 1 hour. After irradiation, 0.01 mL of fluorescein diacetate (10 mM in DMF, Molecular Probes, Eugene, Oreg.) was combined with 2.25 mL buffer and 1.25 mL of 2.5% agarose and poured over the first agarose layer. Detection was achieved by illumination using a short wavelength UV lamp (UVX, 254 nm) and image capture using a Sony® CCD camera coupled to a Macintosh® computer with NIH Image software obtained from the National Institutes of Health.

Fluorescein diacetate was hydrolyzed to produce fluorescein as the reaction proceeded. The plate then became significantly brighter except in the vicinity of beads that released inhibitors, thereby forming zones of inhibition. Beads at the center of these zones were removed with a hollow glass tube, or a spatula, and washed in methanol/methylene chloride (1:1), or with hot water (80° C.), to remove most of the agarose. After a final rinse in methanol, beads were either retested in a separate assay using the methods described above to confirm activity, or analyzed to determine the relevant compound structures by tag decoding. The tag decoding methodology used is described in WO 94/08051, U.S. patent application Ser. Nos. 08/436,120 and 08/239,302, and Nestler et al.

Example 1

Compound Elution

Figure 1B:
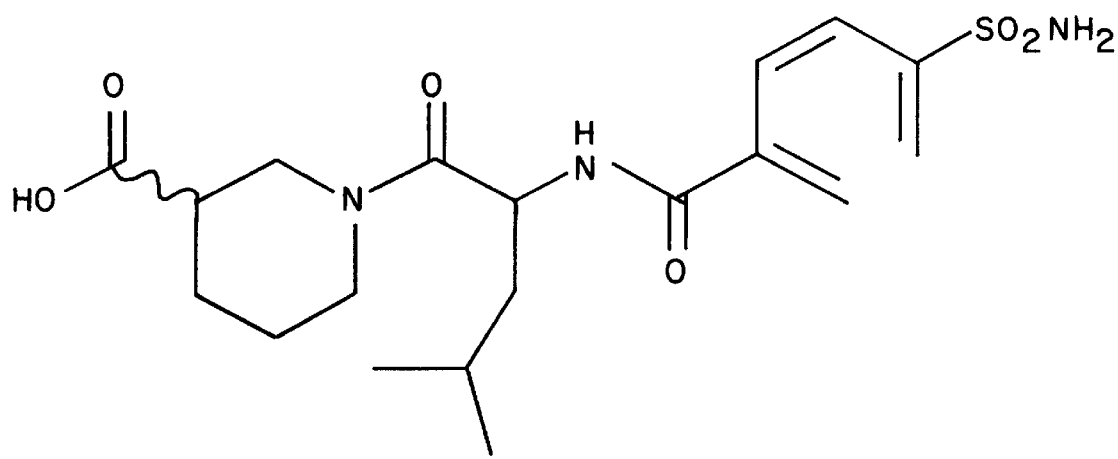
Figures 1C, 4A:
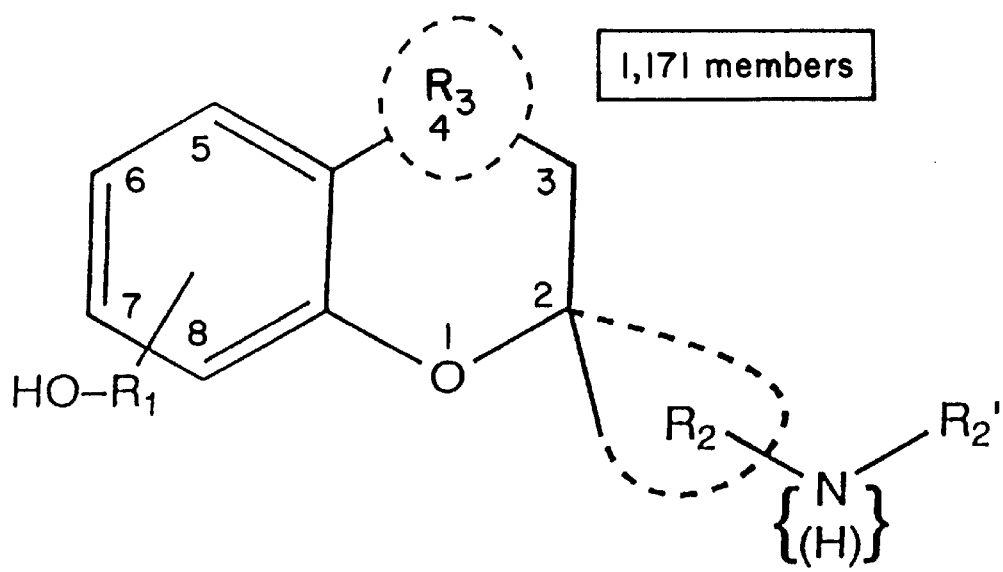
FIGS. 4A, 4B, 4C and 4D show general formulae that encompass two libraries of compounds that were assayed in the Examples. The library encompassed by the formula of FIG. 4A contained 1,171 dihydrobenzopyran compounds. The library encompassed by the formula of FIG. 4B contained 6,727 acylpiperidine compounds.

Compound PC463767 linked to library beads through a photocleavable linker were released, in triplicate, under 365 nm light. Light exposure ranged from 0.5 to 24 hours. Vials each contained 20 beads in 100 µl of acetonitrile. After photoelution, 20 µl of solution containing the photoeluted compound was removed from each vial and analysed by reverse phase HPLC. The amount released over time, in pmol/bead, is shown in FIG. 1. Release was found to be a time dependent event.

Example 2

Assay of Two Known Inhibitors

In this example, two compounds were tested for inhibition of carbonic anhydrase by the lawn assay of the invention. Carbonic anhydrase inhibitors are useful in treating e.g., glaucoma. Results were compared with those obtained using a conventional solution phase assay.

It is known that there is a high correlation between compounds that inhibit binding of dansylamide to carbonic anhydrase and those that inhibit conversion of fluorescein diacetate to fluorescein by carbonic anhydrase. This is believed to result from dansylamide and fluorescein diacetate occupying the same active site (a zinc atom) on carbonic anhydrase. The solution phase assay measured inhibition of dansylamide binding. The lawn assay measured inhibition of the conversion of fluorescein diacetate to fluorescein.

Two aryl sulfonamide-containing compounds (compounds "I" and "II") were synthesized on TentaGel® beads (Rapp Polymere) and assayed in the standard solution-phase assay and in the assay of the invention. Compounds containing aryl sulfonamide substituents are known to be potent inhibitors of carbonic anhydrase. In the solution phase assay, Ki's were determined to be 4 and 660 nM for compounds I and II respectively.

Figure 2A:
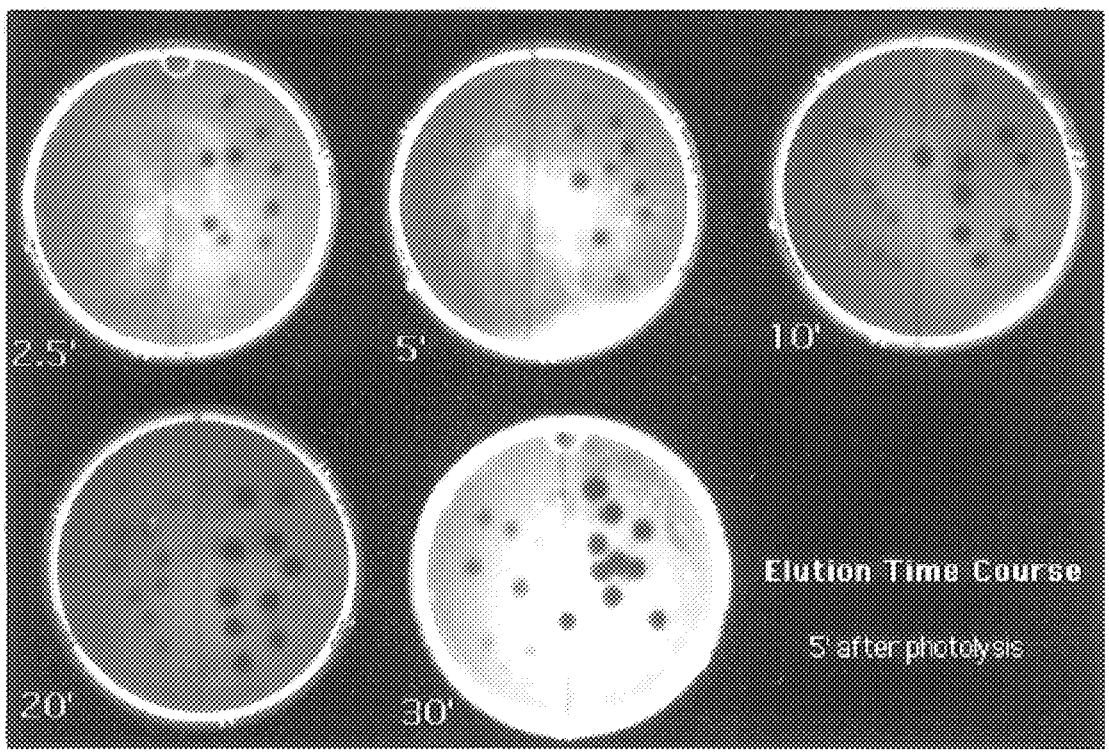
FIGS. 2A–2C show agarose plates having dark zones of inhibition against a fluorescent background caused by two known inhibitors of carbonic anhydrase. The plates were subjected to 2.5, 5, 10, 20 and 30 minutes of photolysis. The zones of inhibition are shown at 5 minutes, 15 minutes, and 30 minutes following photolysis.
Figure 2B:
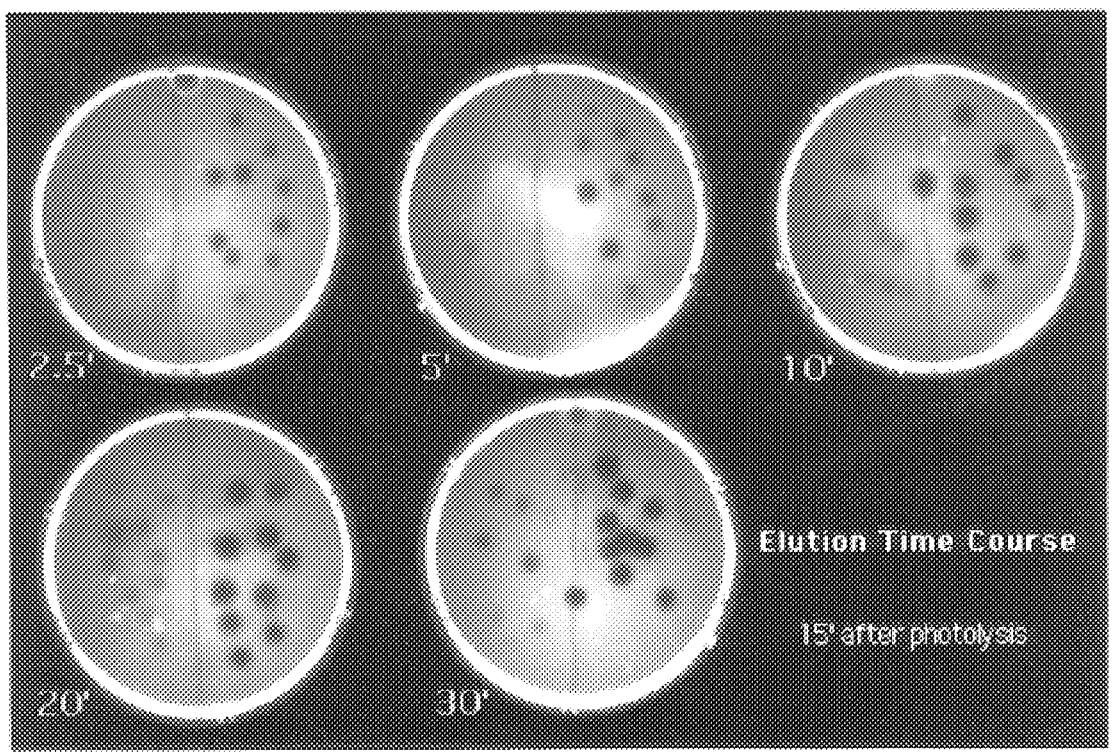
Figure 2C:
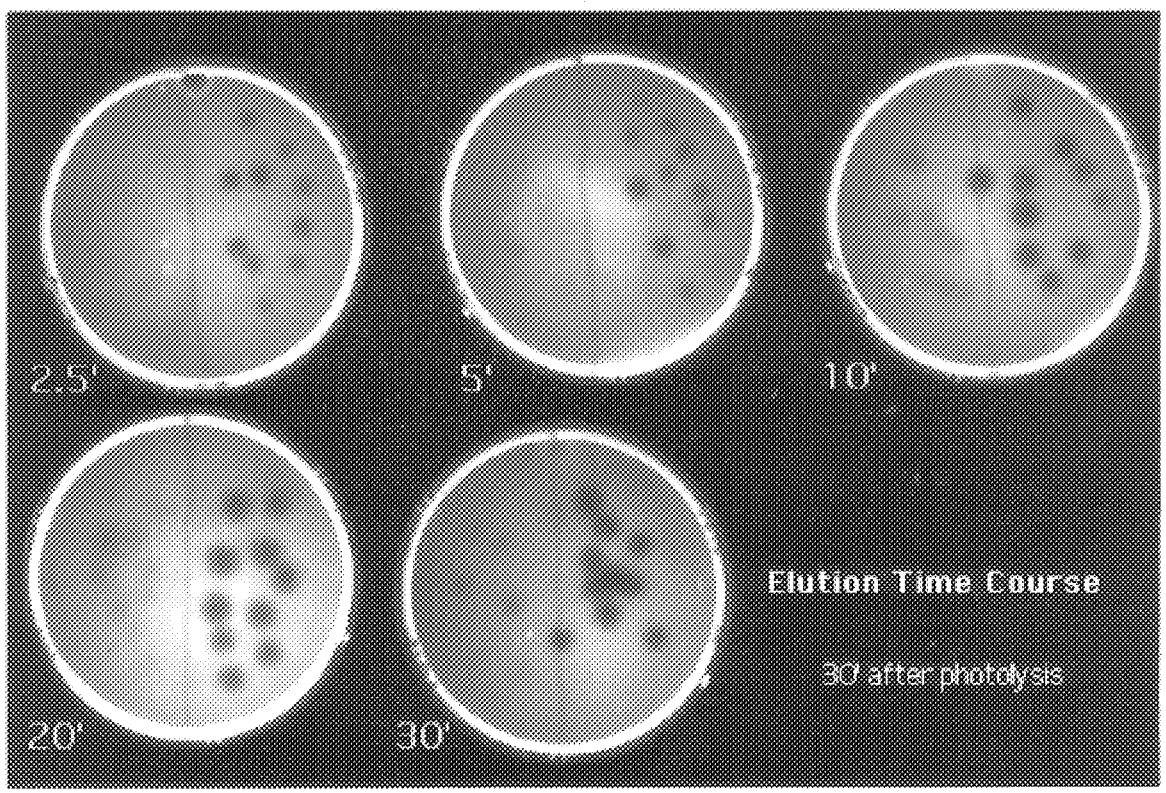

In the assay of the invention, beads containing each compound were embedded in agarose in a series of petri plates. The right side of each plate contained beads with compound 1, and the left side contained beads with compound II. Separate plates were irradiated for 2.5, 5, 10, 20 and 30 minutes. FIGS. 2A–2C respectively show the zones of inhibition that resulted in the plates at 5 minutes, 15 minutes, and 30 minutes following photolysis. The more potent inhibitor of carbonic anhydrase (compound 1) showed a clear zone of inhibition after only 2.5 minutes of photolysis. The weaker inhibitor (compound II) caused only a weak zone of inhibition after five minutes of photolysis. Ten minutes of photolysis was required to obtain a distinct zone. The clearest zones of inhibition were observed at the shortest time after photolysis. Zones at five minutes after photolysis were all sharper than at 15 minutes after photolysis. At 30 minutes after photolysis, all zones were much less distinct; some zones (for compound II) had disappeared.

Figure 3:
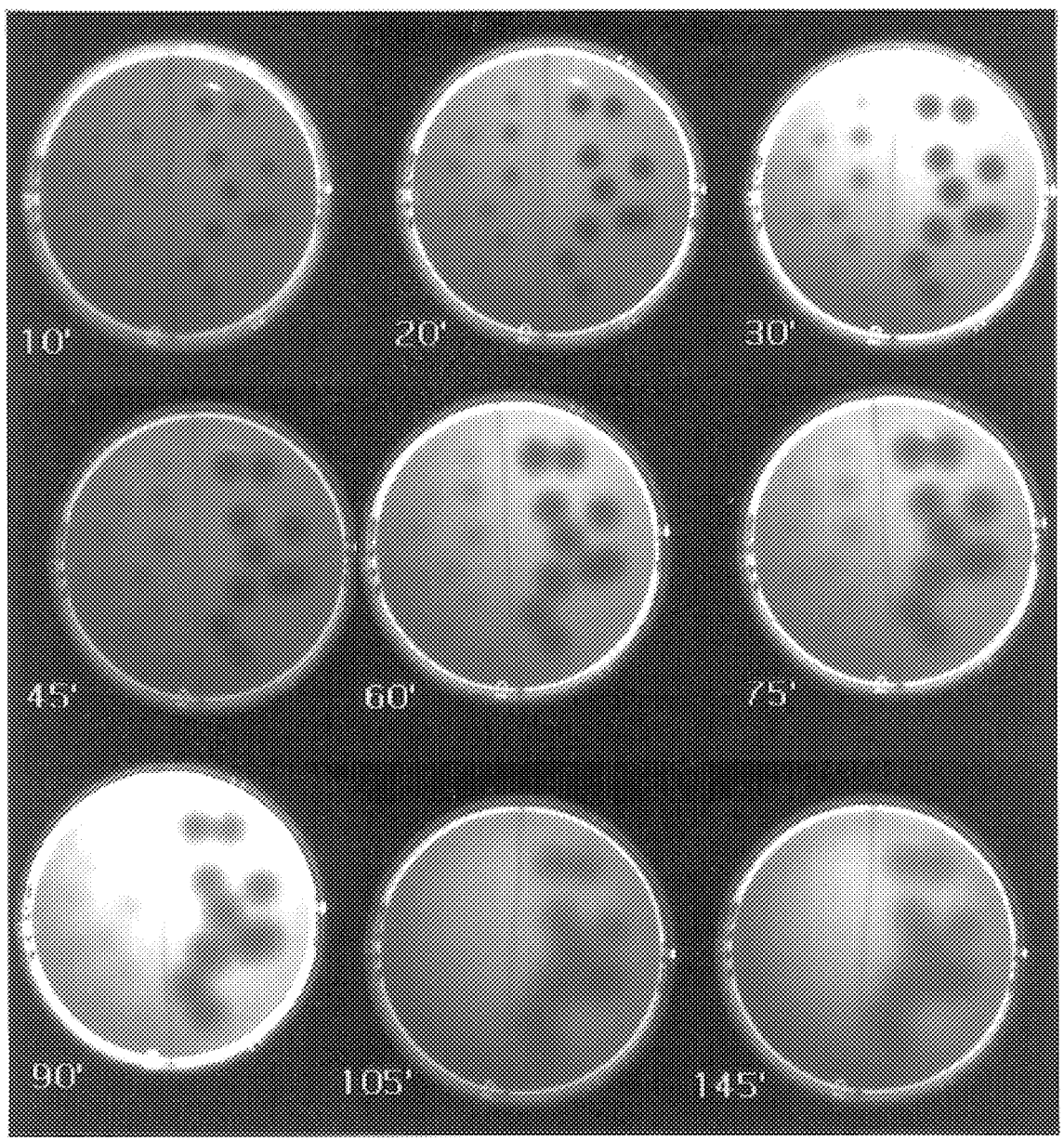
FIG. 3 shows a single plate containing two compounds. The plate was photolysed for 8 minutes and is shown at times from 10 minutes to 145 minutes following photolysis.

In a second experiment, a plate containing beads with compounds I and II was irradiated for a predetermined period of time. The size and duration of the resulting zones of inhibition were determined. Results are shown in FIG. 3. The right side of the plate contained beads with compound 1, and the left side beads with compound II. The zones resulting from compound I were larger than those resulting from compound II. Furthermore, the zones for compound I could be observed for a longer time: signal from compound I persisted for more than two hours (although the zones became very diffuse) while signal for compound II all but disappeared after 90 minutes. In addition, zones of inhibition for compound I were more distinct, i.e., there was greater contrast between the zones and the surrounding areas.

Example 3

Assay of Two Combinatorial Libraries

Figure 4B:
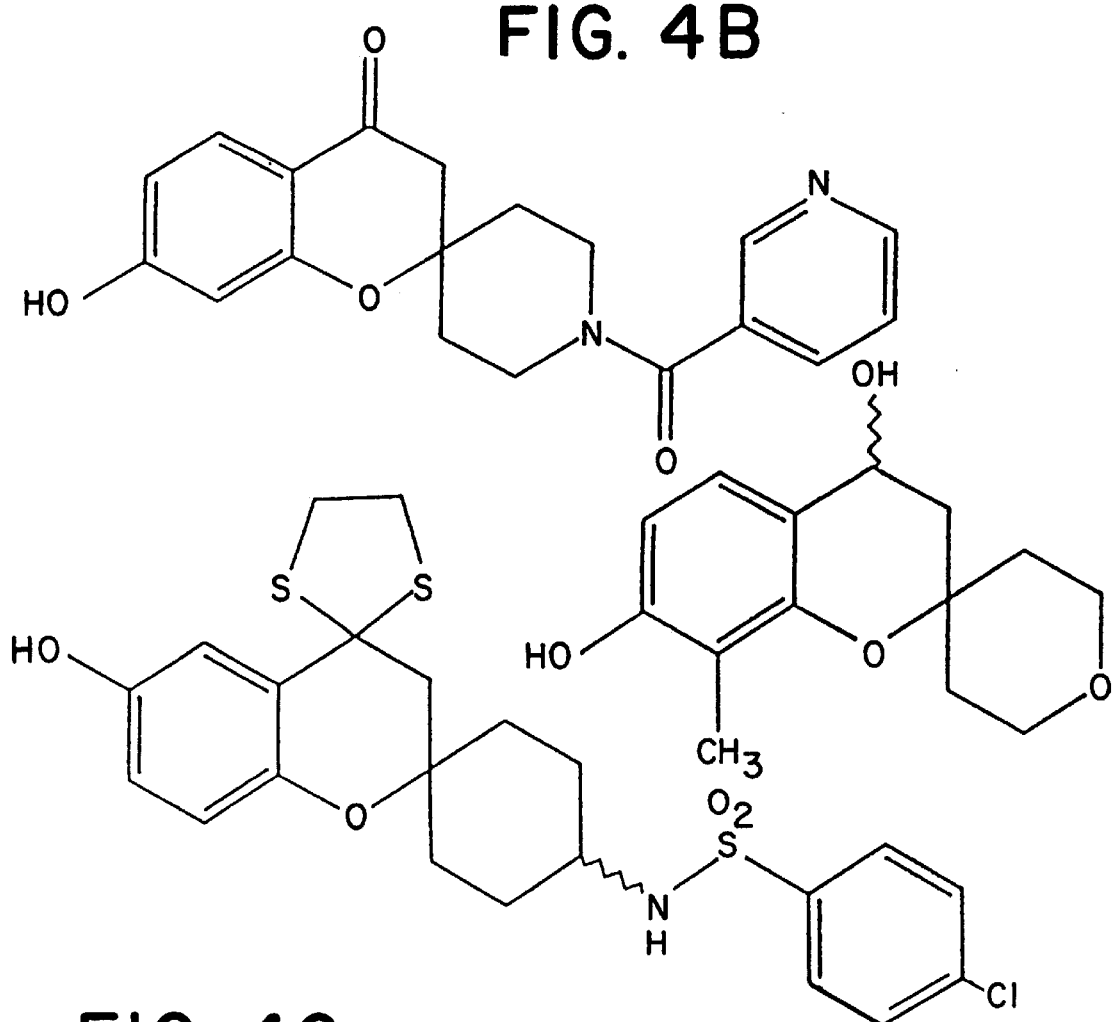
Figure 4C:
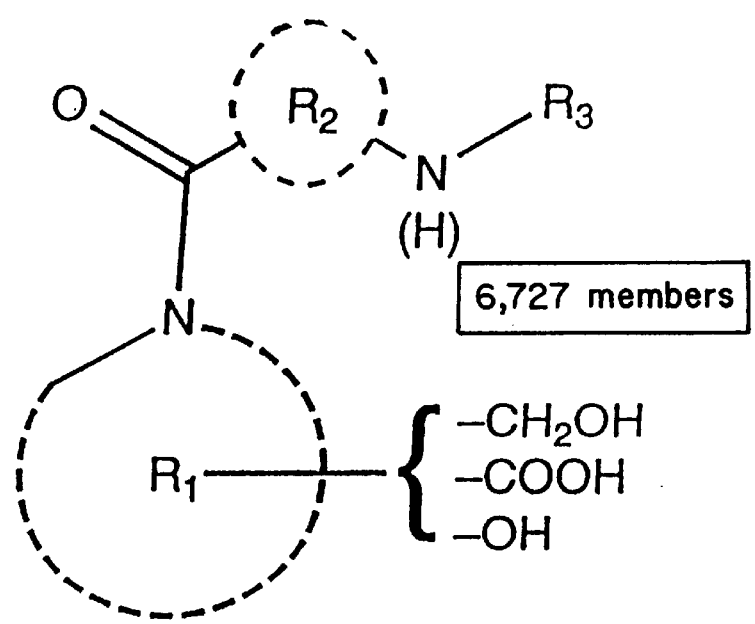
Figure 4D:
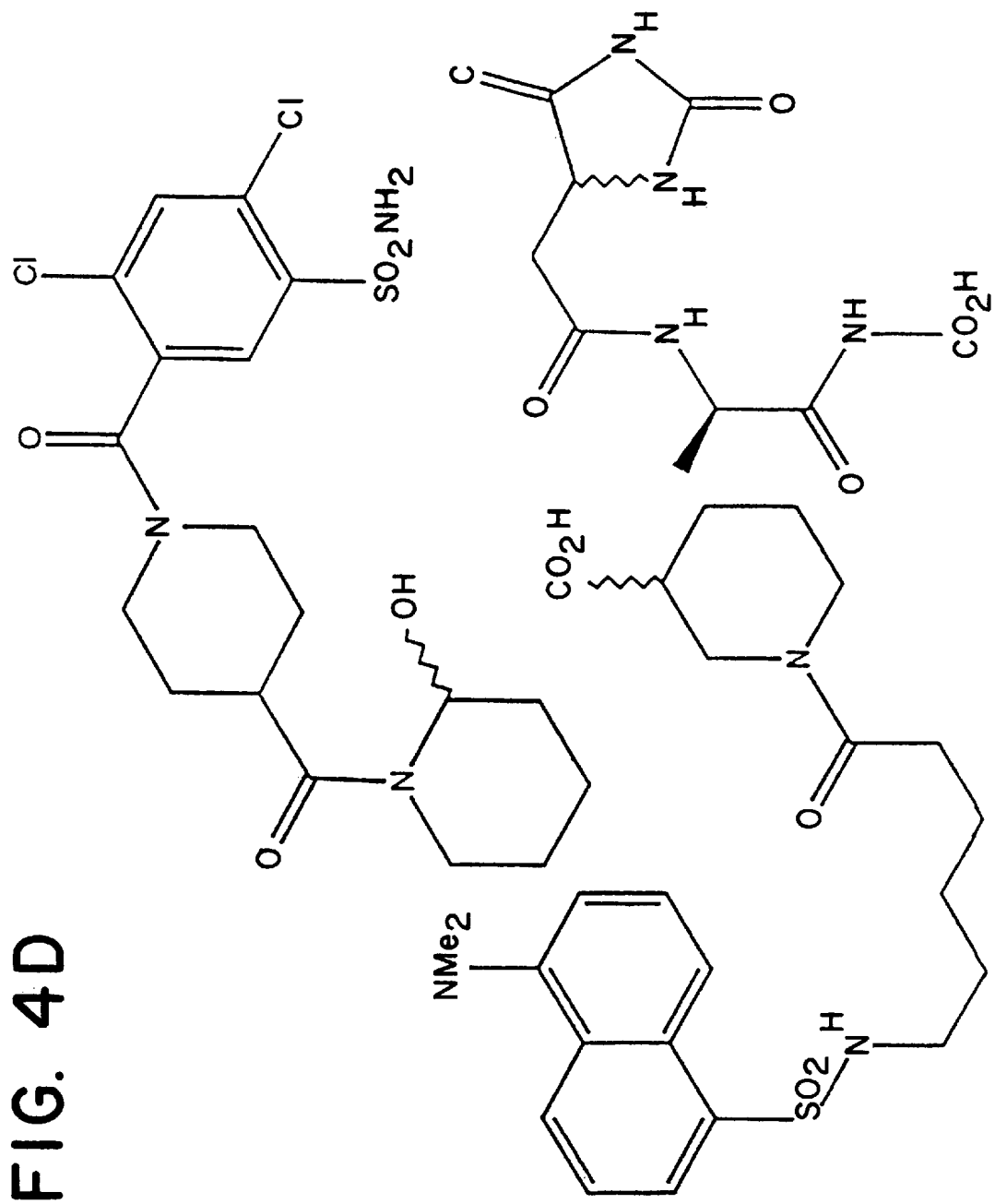

Two combinatorial libraries were evaluated by the assay of the invention for esterase activity in converting fluorescein diacetate to fluorescein. The same libraries were also evaluated by the solution-phase method (for determining displacement of dansylamide). The libraries contained compounds encompassed by the general formulae shown in FIGS. 4A and 4B. The library encompassed by the formula in FIG. 4A contained 1,171 dihydrobenzopyran compounds. The dihydrobenzopyran library contained one aryl sulfonamide substituent at R2' out of 31 possible substituents. The library encompassed by the formula in FIG. 4B contained 6,727 acylpiperidine compounds. The acylpiperidine library was synthesized in two parts. One half of the library (3,472 compounds) contained no aryl sulfonamides. In the other half of the library, three of 15 substitutions at R3 were aryl sulfonamides. These substitutions were a 4-sulfonamide substituted phenyl, a 4-chloro, 3-sulfonamide substituted phenyl, and a 2,4-dichloro, 3-sulfonamide substituted phenyl.

Assays were carried out to identify the most active compounds. In the solution phase assay, dansylamide concentration was increased until only a few members of the library were effective at displacement.

In the assay of the invention, following dispersal of beads in the agarose matrix and photolysis to release compound, enzyme inhibitors were detected as dark zones surrounding specific beads. As carbonic anhydrase converted fluorescein diacetate (non-fluorescent) to fluorescein (fluorescent), the agarose matrix increased significantly in fluorescence intensity. Inhibitors released from beads prevented this conversion and thus caused a dark zone of inhibition around the bead. Beads were then removed for reassay or for decoding. Reassay was necessary if more than one bead was detected at the center of the zone of inhibition.

The amount of photolysis was adjusted to 5 seconds. At this duration, only a few compounds were released in sufficient quantity to inhibit esterase activity. The result was a concentration-dependent competition between library compounds and substrate.

As noted above, the dihydrobenzopyran library contained one aryl sulfonamide substituent at R2' out of 31 possibilities, amounting to about 3% of the library. Using the assay of the invention, approximately 3% of the compounds were found to be active. Decoding indicated that all of the active compounds were aryl sulfonamides. The most active aryl sulfonamides in the lawn assay were found to be very similar in structure to those found to be most active in the solution-phase assay. Reducing the amount of dansylamide was not found to effectively distinguish the most active compounds in either assay.

When the library of acylpiperidine compounds was assayed according to the invention, no active compounds were found in the part of the library that contained no aryl sulfonamide substitutions. Similarly, no compounds in this part of the library were found to be active using the solution-phase assay. In the other half of the library, 25% of the compounds containing aryl sulfonamides at R3 were found to be active using 20 minutes of photolysis. The same library was also screened using 2 minutes of photolysis, to decrease the level of activity of the compounds. All active structures contained an aryl sulfonamide substitution. The most potent compounds were structurally similar to those that were also found most potent in the solution phase assay. At the shortest photolysis times, 4-sulfonamide substituted compounds predominated among the active compounds. Similarly, in the solution phase assay, the most potent compound contained a 4-sulfonamide substitution. The most active compounds in both the lawn assay and the solution phase assay contained hydrophobic amino acid chains at R2 (i.e., containing valine, leucine and/or phenylalanine residues). In both assays, moderately active compounds contained similar substituents at R2, including glutamine. In both assays, active compounds contained 2 or 3 substituted hydroxymethyl piperidine at the R1 position.

These results showed that the assay of the invention allowed the rapid and accurate detection of enzyme inhibitors released from the libraries of beads.

Example 4

Lawn Assay for Inhibitors of Inositol Monophosphate

An assay of the invention for inhibitors of inositol monophosphate is carried out in the same manner as described above for carbonic anhydrase inhibitors, with the following substitutions: The buffer used is 20 mM Tris, 1 mM EGTA, pH 7.8. The agarose layer contains 1 mg/mL of recombinant human inositol monophosphate, purified from E. coli, and 10 mM $MgCl_2$. The substrate is methylumbelliferyl phosphate (Sigma Chemical Company, St. Louis Mo., M-8883), CSPD (Tropix, Bedford Mass.) or CDP-Star (Tropix). CSPD and CDP-Star are chemiluminescent substrates. The preferred substrate is CSPD. Inositol monophosphate is believed to be the molecular target of Lithium therapy in bipolar disease.

Example 5

Lawn Assay for Compounds that Affect Tyrosine Phosphatase

An assay of the invention chromogenically assays compounds for their affect on the catalytic domain of human SHPTP1, a protein tyrosine phosphatase (D. Pei et al. (1993) PNAS 90, 1092) using p-nitrophenylphosphate as a substrate. This enzyme is assayed as described above for carbonic anhydrase, with the following substitutions. The buffer used is 100 mM N,N-bis(2-hydroxyethyl)glycine, pH 8. The first (lower) agarose layer contains 0.5 mg/mL recombinant human SHPTP1 catalytic domain, purified from E. coli, and the substrate is 4-nitrophenyl phosphate (Sigma Chemical Corp.). Enzyme activity corresponds with the release of the 4-nitrophenolate anion ($\lambda_{max}$ 400 nm, $\epsilon$ 18,300 $M^{-1}$ $cm^{-1}$), which appears as a yellow color on a clear background. Areas where affectors of the SHPTP1 catalytic domain are found are distinguished by either clear zones of inhibition or more colored zones of stimulation.

What is claimed is:

1. A lawn assay for identifying compounds that affect an enzymatic reaction, said assay comprising the steps of:
   a) providing an enzyme;
   b) further providing a substrate for the enzyme and optionally a coenzyme for said enzyme;
   c) providing a plurality of solid supports, wherein each support comprises multiple copies of a compound attached thereto by a cleavable linker, said compound to be screened for its effect on said enzymatic reaction;

d) contacting said solid supports with a first colloidal matrix and cleaving at least a portion of said multiple copies from said supports, either before or after said contacting, so that said compound diffuses into said matrix;

e) carrying out said enzymatic reaction; and f) monitoring a photometrically detectable change in said substrate, or said coenzyme to determine a zone of activity in said matrix associated with one or more of said supports to idientify one or more compounds that affect said enzymatic reaction, wherein said enzyme is dispersed in said first colloidal matrix, and wherein said substrate is dispersed in a second colloidal matrix, and optionally wherein said coenzyme is dispersed in said first or second matrix, and wherein said step of carrying out said enzymatic reaction comprises, following said step of contacting said solid supports to said first colloidal matrix, and following said cleaving of at least a portion of said multiple copies from said solid supports, contacting said second matrix with said first matrix to allow said substrate to diffuse into said first colloidal matrix.

2. The lawn assay of claim 1 comprising an assay for an enzyme inhibitor.

3. The lawn assay of claim 1 wherein said substrate is selected from the group consisting of a fluorogenic substrate and a fluorescent substrate.

4. The lawn assay of claim 1 wherein said step of contacting comprises embedding said solid supports in said colloidal matrix.

5. The lawn assay of claim 4 wherein said cleaving occurs after said supports are embedded in said colloidal matrix.

6. The lawn assay of claim 1 wherein said cleavable linker is photocleavable, and said cleaving is carried out by exposure to UV light.

7. The lawn assay of claim 1 comprising cleaving said compounds from said supports prior to said step of contacting said solid supports with said first matrix.

8. The lawn assay of claim 1 wherein said solid supports comprise a library of compounds to be screened.

9. A lawn assay for identifying compounds that affect an enzymatic reaction said assay comprising the steps of:

a) providing an enzyme, and a coenzyme for said enzyme;

b) further providing a substrate for the enzyme;

c) providing a plurality of solid supports, wherein each individual support has multiple copies of a compound attached thereto by a cleavable linker, said compound to be screened for its effect on said enzymatic reaction;

d) contacting said solid supports with a first colloidal matrix and cleaving at least a portion of said multiple copies from said supports, either before or after said contacting, so that said copies of said compound diffuses into said matrix;

e) carrying out said enzymatic reaction; and f) photometrically determining a change in absorbance in said coenzyme that results from said enzymatic reaction to determine a zone of activity in said matrix associated with one or more of said supports to identify one or more compounds that affect said enzymatic reaction.

10. A lawn assay according to claim 9 wherein said coenzyme is selected from the group consisting of NADP, NADPH, NAD, and NADH.

11. A lawn assay for identifying compounds that affect enzymatic activity comprising the steps of:

a) providing a first colloidal matrix containing an enzyme and a plurality of solid supports, said solid supports comprising a library of compounds to be screened for their affect on said enzyme's activity, each of said supports having multiple copies of one of said compounds attached thereto through a cleavable linker;

b) providing a substrate for said enzyme and optionally a coenzyme for said enzyme;

c) cleaving at least a portion of said compounds from the solid supports;

d) contacting said substrate with said matrix; and e) carrying out said enzymatic reaction and observing a detectable signal from said substrate, from a reaction product, or from said coenzyme involved in said reaction to determine one or more zones of activity caused by an effect on said enzyme activity by one or more of said compounds to idientify one or more compounds that affect said enzymatic reaction; wherein said substrate is dispersed in a second matrix, wherein step d) comprises contacting said second matrix with said first matrix to allow said substrate to diffuse into said first matrix.

12. The lawn assay of claim 11 comprising an assay for an enzyme inhibitor.

13. The lawn assay of claim 12 wherein said cleavable linker is photocleavable, and said cleaving is carried out by exposure to UV light.

14. The lawn assay of claim 13 wherein said substrate is selected from the group consisting of a fluorogenic substrate and a fluorescent substrate.

15. The lawn assay of claim 13 which comprises determining a change in absorbency in said coenzyme.

16. The lawn assay according to claim 15 wherein said coenzyme is selected from the group consisting of NADP, NADPH, NAD, and NADH.

17. The lawn assay of claim 11 wherein said activity is affected by inhibition of an interaction between a protein which inhibits said enzyme activity and said enzyme, further wherein said protein is contacted with said enzyme to inhibit said enzymatic reaction.

18. The method of claim 11 wherein said colloidal matrix is selected from the group consisting of silica gel, agar, agarose, pectin, polyacrylamide, gelatin, starch, gellan gum and cross-linked dextran.

19. The method of claim 18 wherein said colloidal matrix is low melting agarose in an amount of from 0.5–2.0%, wt/vol.

20. A lawn assay for identifying compounds that are enzyme inhibitors comprising:

a) providing a first layer which is a colloidal matrix containing enzyme, which matrix has embedded therein a mono-layer of solid supports, wherein each individual support has a compound attached through a photocleavable linker, said compound to be screened for inhibitory activity;

b) providing a second layer which is a colloidal matrix and which contains a substrate that can be monitored photometrically during its enzymatic conversion to product;

c) cleaving the linker to release said compound by exposure to UV light;

d) contacting said first layer with said second layer; and e) detecting zones of inhibition of enzymatic activity in said first layer produced thereby to identify one or more compounds that are enzyme inhibitors.

21. The lawn assay of claim 20 wherein said solid supports are selected from the group consisting of beads, pellets, disks, fibers, and gels.

22. The lawn assay of claim 20 wherein said solid supports are polystyrene beads.

* * * * *

UNITED STATES PATENT AND TRADEMARK OFFICE
CERTIFICATE OF CORRECTION

PATENT NO. : 5,856,083

DATED : Jan. 5, 1999

INVENTOR(S) : Chelsky et al.

It is certified that error appears in the above-identified patent and that said Letters Patent is hereby corrected as shown below:

FIG. 1 B

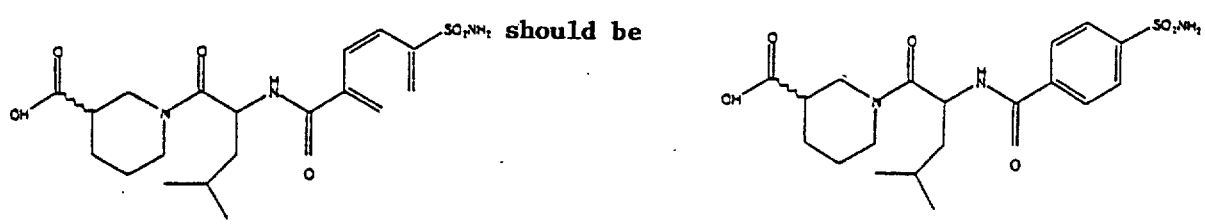

FIG. 4D

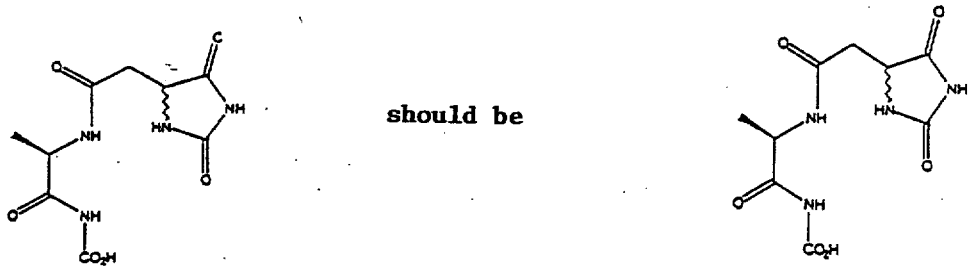

UNITED STATES PATENT AND TRADEMARK OFFICE
CERTIFICATE OF CORRECTION

PATENT NO. : 5,856,083
DATED : Jan. 5, 1999
INVENTOR(S) : Chelsky et al.

It is certified that error appears in the above-identified patent and that said Letters Patent is hereby corrected as shown below:

Column 1, line 34, delete "handing" and insert therefor --handling--.

Column 4, line 45, delete "11" and insert therefor --II--.

Column 8, line 7, delete "to".

Column 9, line 10, delete "C1" and insert therefor --D1--.

Column 12, line 48, delete "1" and insert therefor --I--.

Column 12, line 53, delete "1" and insert therefor --I--.

Column 13, line 1, delete "1" and insert therefor --I--.

Column 15, line 10, delete "idientify" and insert therefor --identify--.

Signed and Sealed this

Twenty-second Day of August, 2000

Attest:

Q. TODD DICKINSON

*Attesting Officer*     *Director of Patents and Trademarks*